(12) United States Patent
Johnson et al.

(10) Patent No.: US 7,070,584 B2
(45) Date of Patent: Jul. 4, 2006

(54) BIOCOMPATIBLE WOUND DRESSING

(75) Inventors: Royce Johnson, Universal City, TX (US); David Tumey, San Antonio, TX (US)

(73) Assignee: KCI Licensing, Inc., San Antonio, TX (US)

(*) Notice: Subject to any disclaimer, the term of this patent is extended or adjusted under 35 U.S.C. 154(b) by 72 days.

(21) Appl. No.: 10/075,743

(22) Filed: Feb. 14, 2002

(65) Prior Publication Data

US 2002/0115952 A1 Aug. 22, 2002

Related U.S. Application Data

(60) Provisional application No. 60/269,957, filed on Feb. 16, 2001.

(51) Int. Cl.
*A61F 13/00* (2006.01)
*A61M 1/00* (2006.01)
*A61M 35/00* (2006.01)

(52) U.S. Cl. ............................ 604/313; 602/41; 602/43; 602/46; 602/48; 604/290; 604/322; 424/444

(58) Field of Classification Search ........ 604/304–308, 604/66, 67, 291, 118, 119, 289, 290, 313, 604/315, 317, 319, 322; 602/41–59; 424/443–449
See application file for complete search history.

(56) References Cited

U.S. PATENT DOCUMENTS

| | | | |
|---|---|---|---|
| 1,355,846 A | 10/1920 | Rannells | |
| 2,547,758 A | 4/1951 | Keeling | |
| 2,632,443 A | 3/1953 | Lesher | |
| 2,682,873 A | 7/1954 | Evans et al. | |
| 2,969,057 A | 1/1961 | Simmons | |
| 3,367,332 A | 2/1968 | Groves | |
| 3,648,692 A | 3/1972 | Wheeler | |
| 3,682,180 A | 8/1972 | McFarlane | |
| 3,826,254 A | 7/1974 | Mellor | |
| 4,080,970 A | 3/1978 | Miller | |
| 4,096,853 A | 6/1978 | Weigand | |

(Continued)

FOREIGN PATENT DOCUMENTS

AU 550575 A1 8/1982

(Continued)

OTHER PUBLICATIONS

Louis C. Argenta, MD and Michael J. Morykwas, PHD; Vacuum-Assisted Closure: A New Method for Wound Control and Treatment: Clinical Experience; Annals of Plastic Surgery, vol. 38, No. 6, Jun. 1997, pp. 563-577; Lippincott Williams & Wilkins, Inc., Philadelphia, PA, U.S.A.

(Continued)

*Primary Examiner*—Kim M. Lewis

(57) ABSTRACT

A biocompatible wound dressing comprised of a pad for insertion substantially into a wound site and a wound drape for sealing enclosure of the foam pad at the wound site. The pad, comprised of a foam or other like material having relatively few open cells in contact with the areas upon which cell growth is to be encouraged so as to avoid unwanted adhesions, but having sufficiently numerous open cells so that drainage and negative pressure therapy may continue unimpaired, is placed in fluid communication with a vacuum source for promotion of fluid drainage, as known in the art. The pad is further comprised of an ultra-low density fused-fibrous ceramic, or a bioabsorbable branched polymer, or cell growth enhancing matrix or scaffolding.

12 Claims, 1 Drawing Sheet

U.S. PATENT DOCUMENTS

| | | |
|---|---|---|
| 4,139,004 A | 2/1979 | Gonzalez |
| 4,165,748 A | 8/1979 | Johnson |
| 4,233,969 A | 11/1980 | Lock et al. |
| 4,245,630 A | 1/1981 | Lloyd et al. |
| 4,261,363 A | 4/1981 | Russo |
| 4,275,721 A | 6/1981 | Olson |
| 4,284,079 A | 8/1981 | Adair |
| 4,333,468 A | 6/1982 | Geist |
| 4,373,519 A | 2/1983 | Errede et al. |
| 4,382,441 A | 5/1983 | Svedman |
| 4,392,853 A | 7/1983 | Muto |
| 4,392,858 A | 7/1983 | George et al. |
| 4,419,097 A | 12/1983 | Rowland |
| 4,475,909 A | 10/1984 | Eisenberg |
| 4,480,638 A | 11/1984 | Schmid |
| 4,525,166 A | 6/1985 | Lecerc |
| 4,525,374 A | 6/1985 | Vailancourt |
| 4,540,412 A | 9/1985 | Van Overloop |
| 4,543,100 A | 9/1985 | Brodsky |
| 4,551,139 A | 11/1985 | Plaas et al. |
| 4,569,348 A | 2/1986 | Hasslinger |
| 4,605,399 A | 8/1986 | Weston et al. |
| 4,608,041 A | 8/1986 | Nielsen |
| 4,614,794 A * | 9/1986 | Easton et al. ............... 530/356 |
| 4,640,688 A | 2/1987 | Hauser |
| 4,655,754 A | 4/1987 | Richmond et al. |
| 4,733,659 A | 3/1988 | Edenbaum et al. |
| 4,743,232 A | 5/1988 | Kruger |
| 4,787,888 A | 11/1988 | Fox |
| 4,826,949 A | 5/1989 | Stanko |
| 4,838,883 A | 6/1989 | Matsuura |
| 4,840,187 A | 6/1989 | Brazler |
| 4,863,449 A | 9/1989 | Therriault et al. |
| 4,872,450 A | 10/1989 | Austad |
| 4,878,901 A | 11/1989 | Sachse |
| 4,897,081 A | 1/1990 | Poirier et al. |
| 4,906,233 A | 3/1990 | Moriuchi et al. |
| 4,906,240 A | 3/1990 | Reed et al. |
| 4,919,654 A | 4/1990 | Kalt |
| 4,941,882 A | 7/1990 | Ward et al. |
| 4,953,565 A | 9/1990 | Tachibana et al. |
| 4,969,880 A | 11/1990 | Zamierowski |
| 4,985,019 A | 1/1991 | Michelson |
| 5,037,397 A | 8/1991 | Kalt et al. |
| 5,100,396 A | 3/1992 | Zamierowski |
| 5,149,331 A | 9/1992 | Ferdman et al. |
| 5,167,613 A | 12/1992 | Karami et al. |
| 5,176,663 A | 1/1993 | Svedman et al. |
| 5,232,453 A | 8/1993 | Plass et al. |
| 5,256,418 A | 10/1993 | Kemp et al. |
| 5,261,893 A | 11/1993 | Zamierowski |
| 5,298,015 A | 3/1994 | Komatsuzaki et al. |
| 5,344,415 A | 9/1994 | DeBusk et al. |
| 5,358,494 A | 10/1994 | Svedman |
| 5,449,383 A | 9/1995 | Chatelier et al. |
| 5,527,293 A | 6/1996 | Zamierowski |
| 5,556,375 A | 9/1996 | Ewall |
| 5,578,662 A | 11/1996 | Bennett et al. |
| 5,607,388 A | 3/1997 | Ewall |
| 5,621,035 A * | 4/1997 | Lyles et al. ............... 524/404 |
| 5,629,186 A | 5/1997 | Yasukawa et al. |
| 5,636,643 A | 6/1997 | Argenta et al. |
| 5,645,081 A | 7/1997 | Argenta et al. |
| 5,780,281 A | 7/1998 | Yasukawa et al. |
| 5,795,584 A | 8/1998 | Totakura et al. |
| 5,902,874 A | 5/1999 | Roby et al. |
| 5,902,875 A | 5/1999 | Roby et al. |
| 5,914,387 A | 6/1999 | Roby et al. |
| 5,951,295 A | 9/1999 | Lyles et al. |
| 5,997,568 A | 12/1999 | Liu |
| 6,071,267 A | 6/2000 | Zamierowski |
| 6,135,116 A | 10/2000 | Vogel et al. |
| 6,488,643 B1 | 12/2002 | Tumey et al. |
| 6,493,568 B1 | 12/2002 | Bell et al. |
| 2002/0115951 A1 | 8/2002 | Norstrem et al. |
| 2002/0120185 A1 | 8/2002 | Johnson |
| 2002/0143286 A1 | 10/2002 | Tumey |
| 2003/0077311 A1 * | 4/2003 | Vyakarnam et al. ........ 424/426 |

FOREIGN PATENT DOCUMENTS

| | | |
|---|---|---|
| EP | 01000148 | 2/1984 |
| WO | 96/05873 | * 2/1996 |

OTHER PUBLICATIONS

Susan Mendez-Eastman, RN; When Wounds Won't Heal, RN Jan. 1998, vol. 61(1); Medical Economics Company, Inc., Montvale, NJ, USA.

James H. Blackburn II, MD et al.; Negative-Pressure Dressings as a Bolster for Skin Grafts; Annals of Plastic Surgery, vol. 40, No. 5, May 1998, pp. 453-457; Lippincott Williams & Wilkins, Inc., Philidelphia, PA, USA.

John Masters; Letter to the editor; British Journal of Plastic Surgery, 1998, vol. 51(3), p. 267: Elsevier Science/The British Assocition of Plastic Surgeons, United Kingdom.

S.E. Greer, et al.; The Use of Subatmospheric Pressure Dressing Therapy to Clos Lymphocutaneous Fistulas of the Groin; British Journal of Plastic Surgery (2000), 53, p. 484-487, Article No. BJPS2000.3360, Elsevier Science/The British Association of Plastic Surgeons, United Kingdom.

George V. Letsou, M.D., et al. ; Stimulation of Adenylate Cyclase Activity in Cultured Endothelial Cells Subjected to Cyclic Stretch; Journal of Cardiovascular Surgery, 31, 1990, pp. 634-639; Edlzonla Minerva Medica, Torino, Italy.

* cited by examiner

BIOCOMPATIBLE WOUND DRESSING

The application claims the benefit under 35 U.S.C. § 119(e) of U.S. provisional patent application No. 60/269,657, filed Feb. 16, 2001.

FIELD OF THE INVENTION

This invention relates generally to wound dressings commonly associated with the vacuum induced healing of open wounds. More particularly, the present invention relates to a wound dressing, having a cell growth enhancing porous lattice, matrix, or scaffold, or a bioabsorbable layer as part of the dressing to enhance the wound healing.

BACKGROUND OF THE INVENTION

Vacuum induced healing of open wounds has recently been popularized by Kinetic Concepts, Inc. of San Antonio, Tex., by its commercially available V.A.C.® product line. The vacuum induced healing process has been described in commonly assigned U.S. Pat. No. 4,969,880 issued on Nov. 13, 1990 to Zamierowski, as well as its continuations and continuations in part, U.S. Pat. No. 5,100,396, issued on Mar. 31, 1992, U.S. Pat. No. 5,261,893, issued Nov. 16, 1993, and U.S. Pat. No. 5,527,293, issued Jun. 18, 1996, the disclosures of which are incorporated herein by this reference. Further improvements and modifications of the vacuum induced healing process are also described in U.S. Pat. No. 6,071,267, issued on Jun. 6, 2000 to Zamierowski and U.S. Pat. Nos. 5,636,643 and 5,645,081 issued to Argenta et al. on Jun. 10, 1997 and Jul. 8, 1997 respectively, the disclosures of which are incorporated by reference as though fully set forth herein.

Substantial work has also been performed relating to the creation of bioabsorbable and includable, cell growth enhancing matrices, lattices, or scaffolds. Exemplary U.S. patents known to applicant include Kemp et al. U.S. Pat. No. 5,256,418 issued Oct. 26, 1993; Chatelier et al. U.S. Pat. No. 5,449,383 issued Sep. 12, 1995; Bennett et al. 5,578,662 issued Nov. 26, 1996; and two patents issued to Yasukawa et al. U.S. Pat. No. 5,629,186 issued May 13, 1997 and U.S. Pat. No. 5,780,281 issued Jul. 14, 1998, both from a common parent application; the disclosures of which are incorporated by reference herein.

As is well known to those of ordinary skill in the art, closure of surface wounds involves the inward migration of epithelial and subcutaneous tissue adjacent the wound. This migration is ordinarily assisted through the inflammatory process, whereby blood flow is increased and various functional cell types are activated. Through the inflammatory process, blood flow through damaged or broken vessels is stopped by capillary level occlusion; thereafter, cleanup and rebuilding operations may begin. Unfortunately, this process is hampered when a wound is large or has become infected. In such wounds, a zone of stasis (i.e. an area in which localized swelling of tissue restricts the flow of blood to the tissues) forms near the surface of the wound.

Without sufficient blood flow, the epithelial and subcutaneous tissues surrounding the wound not only receive diminished oxygen and nutrients, but also are also less able to successfully fight bacterial infection and thus are less able to naturally close the wound. Until the advent of vacuum induced therapy, such difficult wounds were addressed only through the use of sutures or staples. Although still widely practiced and often effective, such mechanical closure techniques suffer a major disadvantage in that they produce tension on the skin tissue adjacent the wound. In particular, the tensile force required in order to achieve closure using sutures or staples may cause very high localized stresses at the suture or staple insertion point. These stresses commonly result in the rupture of the tissue at the insertion points, which can eventually cause wound dehiscence and additional tissue loss.

Additionally, some wounds harden and inflame to such a degree due to infection that closure by stapling or suturing is not feasible. Wounds not reparable by suturing or stapling generally require prolonged hospitalization, with its attendant high cost, and major surgical procedures, such as grafts of surrounding tissues. Examples of wounds not readily treatable with staples or suturing include large, deep, open wounds; decubitus ulcers; ulcers resulting from chronic osteomyelitis; and partial thickness burns that subsequently develop into full thickness burns.

As a result of these and other shortcomings of mechanical closure devices, methods and apparatus for draining wounds by applying continuous negative pressures have been developed. When applied over a sufficient area of the wound, such negative pressures have been found to promote the migration toward the wound of epithelial and subcutaneous tissues. In practice, the application to a wound of negative gauge pressure, commercialized by Assignee or its parent under the designation "Vacuum Assisted Closure" (or "V.A.C.®") therapy, typically involves the mechanical-like contraction of the wound with simultaneous removal of excess fluid. In this manner, V.A.C.® therapy augments the body's natural inflammatory process while alleviating many of the known intrinsic side effects, such as the production of edema caused by increased blood flow absent the necessary vascular structure for proper venous return.

While V.A.C.® therapy has been highly successful in the promotion of wound closure, healing many wounds previously thought largely untreatable, some difficulty remains. Because the very nature of V.A.C.® therapy dictates an atmospherically sealed wound site, the therapy must often be performed to the exclusion of other beneficial, and therefore desirable, wound treatment modalities. One of these hitherto excluded modalities is the encouragement of cell growth by the provision of an in situ cell growth-enhancing matrix.

Additional difficulty remains in the frequent changing of the wound dressing. As the wound closes, binding of cellular tissue to the wound dressing may occur. Use of traditional V.A.C.® therapy necessitates regular changing of the dressing. Reckless dressing changes can result in some tissue damage at the wound site if cellular tissue has grown excessively into the dressing.

Accordingly a primary object of the present invention is to provide an improved wound dressing for vacuum induced healing therapy, which overcomes the problems and limitations of the prior art.

A further object of the present invention is to provide a dressing that is also readily adaptable to a variety of wound sizes and shapes and that requires no inordinate modification of known procedures for administration of V.A.C.® therapy.

Another object is to provide a pad that enables the concurrent application of vacuum induced healing and cell growth enhancement in the treating of a wound by providing a bioabsorbable, or includable, porous cell growth enhancing matrix substrate thereupon.

An additional object of the present invention is to allow for controlled application of growth factors or other healing factors, which could be embedded in the dressing or introduced into the dressing through a port or other connector fitting.

Still another object of the present invention is to provide a fully and/or partially bioabsorbable wound dressing that minimizes disruption of the wound site during dressing changes.

A yet further object of the present invention is to provide such a dressing that is economical and disposable, but also safe for general patient use.

SUMMARY OF THE INVENTION

In accordance with the foregoing objects, the present invention generally comprises a foam pad for insertion substantially into the wound site and a wound drape for sealing enclosure of the foam pad at the wound site. The foam pad, comprised of a foam having relatively few open cells in contact with the areas upon which cell growth is to be encouraged so as to avoid unwanted adhesions, but having sufficiently numerous open cells so that drainage and V.A.C.® therapy may continue unimpaired, is placed in fluid communication with a vacuum source for promotion of fluid drainage, as known in the art. The foam pad is further comprised of a cell growth lattice, matrix, or scaffolding, all of which have been used in the art to describe similar constructs, is noninvasive to the known V.A.C.® therapy and requires no modification thereof. Additionally, or alternatively, the foam pad may be comprised of bioabsorbable polymers.

The foam pad of the present invention is provided with a bioabsorbable, or includable, fibrous growth-enhancing matrix. Numerous suitable materials for this purpose are known to the art, including collagen, dissolvable nylon, soluble plastics, and fibrous ceramic material. An exemplary fibrous ceramic material that may be utilized is an ultra-low density fused-fibrous ceramic manufactured by Materials Evolution and Development USA, Inc., under the trade name P.R.I.M.M.™ (Polymeric Rigid Inorganic Matrix Material), and further described in U.S. Pat. No. 5,951,295 issued on Sep. 14, 1999 to Lyles, et al., which is incorporated herein by reference. Additional materials may include alginates, fibrin gels, fused fibers and other similar materials utilized by those skilled in the art, that are capable of providing an invadable space and scaffolding for cellular growth. Alternatively, the growth-enhancing matrix may be non-fibrous, such as a gel-like growth-enhancing matrix. This matrix comprises a cell growth enhancing substrate that is up to over 90% open space. The fibers, or other particles, and spaces create nooks and crannies that provide an excellent environment to enhance cell growth, and thus further the process envisioned by the vacuum induced healing process.

Upon placement of the pad, having the cell growth enhancing substrate matrix embedded therein, an airtight seal is formed over the wound site to prevent vacuum leakage. In use the V.A.C.® therapy is conducted as known and, if desired, cell growth enhancement therapy is added by simply placing the matrix on the pad that is located within the wound. Given the addition of a suitable surface to which the fibrous lattice may be attached, the cell growth is channeled into the most desirable form and location, but is kept away from the pad itself. Utilization of bioabsorbable branched polymers in the pad itself, in addition to, or in place of the cell growth enhancing matrix, can allow the pad to remain in place during the healing process. As cell growth continues, the pad is absorbed, and there is no need to remove the pad.

An alternative embodiment comprises use of bioabsorbable branched polymers within a layer of the pad adjacent the wound, such that upon removal of the pad during dressing changes, the bioabsorbably branched polymer layer is left behind, leaving the wound site itself undisturbed. Additionally, the cell growth enhancing substrate matrix may be incorporated within the polymer layer to further enhance cellular growth at the wound site.

Accordingly, cell growth enhancement therapy may be conveniently combined with existing V.A.C.® therapies, without loss of V.A.C.® therapy performance and without inconvenience or overly increased cost.

Finally, many other features, objects and advantages of the present invention will be apparent to those of ordinary skill in the relevant arts, especially in light of the foregoing discussions and the following drawings and exemplary detailed description.

BRIEF DESCRIPTION OF THE DRAWINGS

These and other features and advantages of the invention will now be described with reference to the drawings of certain preferred embodiments, which are intended to illustrate and not to limit the invention, and wherein like reference numbers refer to like components, and in which.

DETAILED DESCRIPTION OF THE PREFERRED EMBODIMENT

Figure 1:
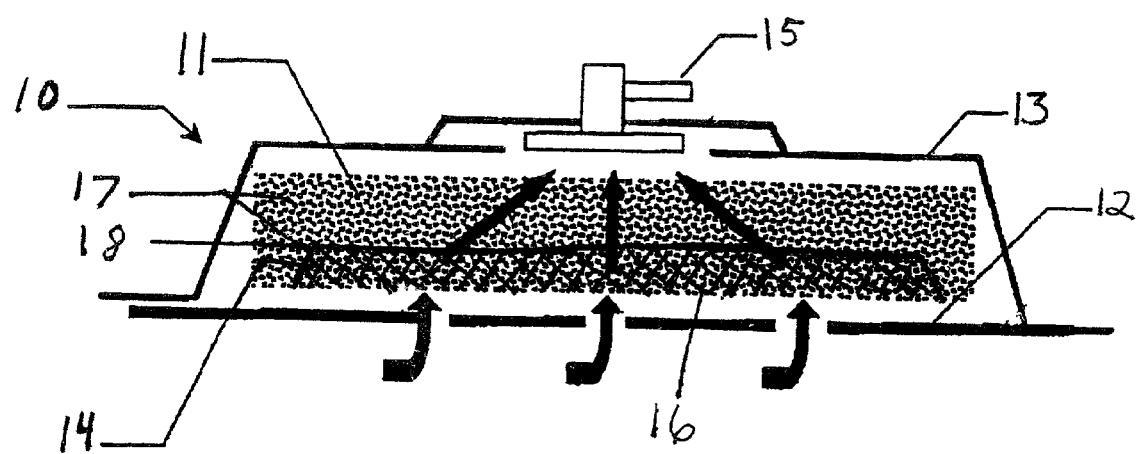
FIG. 1 shows, in partially cut away perspective view, the preferred embodiment of the present invention as applied to a mammalian wound site.

Although those of ordinary skill in the art will readily recognize many alternative embodiments, especially in light of the illustrations provided herein, this detailed description is exemplary of the preferred embodiment of the present invention, the scope of which is limited only by the claims that may be drawn hereto.

The present invention is a biocompatible wound dressing for use with negative pressure therapy. The term "wound" as used herein, may include burns, incisional wounds, excisional wounds, ulcers, traumatic wounds, and chronic open wounds. As used herein, the term "pad" refers to foam, screens, other porous-like materials. The term "conventional pad" refers to polyurethane (PU) or polyvinylalcohol (PVA) foams commonly used with V.A.C.® therapy. The term "V.A.C.® therapy" as used herein, refers to negative pressure wound therapy as commercialized by the assignee or its parent, and further described in the aforementioned patents and patent applications.

Referring now to the figures, the present invention 10 is shown to generally comprise a foam pad 11 for insertion substantially into the wound site 12 and a wound drape 13 for sealing enclosure of the foam pad 11 at the wound site 12. According to the invention, the foam pad 11 is modified to contain a cell growth-enhancing matrix, or lattice 14, whereby a desired highly porous cell growth enhancing substrate may be directed into and about the wound site 12. After insertion into the wound site 12 and sealing with the wound drape 13, the foam pad 11 is placed in fluid communication with a vacuum source for promotion of fluid drainage, as known to those of ordinary skill in the art. Foam pad 11 is modified from prior art pads in that the pad 11 comprises matrix 14 that is noninvasive to the known V.A.C.® therapy and therefore requires no modification thereof.

According to the preferred embodiment of the present invention, the foam pad 11, wound drape 13 and vacuum source are implemented as known in the prior art, with the exception of those modifications to the foam pad 11 detailed further herein. Each of these components is detailed in U.S. patent application Ser. No. 08/951,832 filed Oct. 16, 1997, which is a Continuation of U.S. patent application Ser. No. 08/517,901 filed Aug. 22, 1995, which is a Continuation-in-part of U.S. patent application Ser. No. 08/293,854 filed Aug. 22, 1994. By this reference, the full specification of U.S. patent application Ser. No. 08/951,832 ("the '832 application"), including the claims and the drawings, is incorporated as though fully set forth herein.

As detailed in the '832 application, the foam pad 11 preferably comprises a highly reticulated, open-cell polyurethane or polyether foam for good permeability of wound fluids while under suction. As also detailed in the '832 application, the foam pad 11 is preferably placed in fluid communication, via a plastic or like material hose 15, with a vacuum source, which preferably comprises a canister safely placed under vacuum through fluid communication, via an interposed hydrophobic membrane filter, with a vacuum pump. Finally, the '832 application also details the wound drape 13, which preferably comprises an elastomeric material at least peripherally covered with a pressure sensitive, acrylic adhesive for sealing application over the wound site 12.

According to the preferred method of the present invention, those components as are described in the '832 application are generally employed as known in the art with the exception that the foam pad 11 is provided with a matrix 14. This matrix 14 is shown to comprise porous material 16 that has been formed into a plurality of sections 17. The material 16 is implanted in the foam pad 11 at the base 18 of the pad 11. Because it is necessary to trim the foam pad 11 in preparation for V.A.C.® therapy wound treatment, material 16 preferably is placed in the central portion of pad 11. Applicant does not intend to limit itself to a regular or symmetrical arrangement of material 16 or sections 17 by use of the term "matrix".

Alternatively, or in addition to the preferred embodiment, the foam pad may be comprised of bioabsorbable branched polymers alone (not shown), or in combination with the matrix 14.

Upon placement of the pad 11, having the matrix 14 embedded therein, and/or protruding therefrom, and/or comprised of bioabsorbable branched polymers, the wound drape 13 is applied over the pad to form an airtight seal over the wound site. In use, the V.A.C.® therapy is conducted as known and, if desired, cell growth enhancement therapy is added by simply providing the matrix 14 comprising material 16. In this manner, cell growth enhancement therapy may be conveniently combined with existing V.A.C.® therapies, without loss of V.A.C.® therapy performance and without inconvenience or overly increased cost.

EXAMPLE I

The above described open celled foam is formed into a pad. The general principles set forth in U.S. Pat. No. 5,795,584 issued to Totakura et al on Aug. 18, 1998 at Col. 5 lines 5–42, are followed to create a structure superimposed on the bottom of the pad. Holes are placed in those portions of the non-bioabsorbable substrate relatively remote from the bioabsorbable cell growth enhancing matrix substrate. The matrix covers a portion of the pad located within the boundaries of the wound being treated. The pad is then completely covered by an airtight drape, and subjected to sub atmospheric pressure, as is the standard practice for utilizing V.A.C.® therapy. The matrix is absorbed within the expected useful life of the pad, so, that when the pad is removed, the matrix had been absorbed, and the growing cells are not disturbed. The pad is replaced, if necessary, either by a conventional pad or by a matrix containing pad, as deemed therapeutically necessary.

EXAMPLE II

A conventional pad is selected. A collagen cell growth matrix is applied to a portion of the bottom thereof. The general principles of V.A.C.® therapy are followed, with the matrix containing pad substituted for a conventional pad. During the expected duty cycle of the pad, the collagen matrix is absorbed by the growing cells, so that when the pad is removed, the matrix had been absorbed, and the growing cells are not disturbed. The pad is replaced, if necessary, either by a conventional pad or by a matrix containing pad, as deemed therapeutically necessary.

EXAMPLE III

The procedure set forth in EXAMPLE II is followed. However, an ultra-low density fused-fibrous ceramic, sometimes referred to under the trademark P.R.I.M.M., is substituted for the collagen matrix thereof. The general principles of V.A.C. ® therapy are followed. During the expected duty cycle of the pad, the ultra-low density fused-fibrous ceramic is absorbed by the growing cells, so that when the pad is removed, the ultra-low density fused-fibrous ceramic had been absorbed, and the growing cells were not disturbed. The pad is replaced, if necessary, either by a conventional pad or by a matrix containing pad, as deemed therapeutically necessary.

EXAMPLE IV

Many suitable bioabsorbable materials have been used for sutures, surgical implements, and the like. A small sample of these materials are set forth in the following U.S. patents, to wit: U.S. Pat. No. 5,997,568, issued to Lin on Dec. 7, 1999 and the following patents issued in 1999 to Roby et al.: U.S. Pat. Nos. 5,914,387; 5,902,874 and 5,902,875. A selected one or more of these, or similar materials, are placed upon a conventional pad. The general principles of V.A.C. ® therapy are followed. During the expected duty cycle of the pad, the bioabsorbable material is absorbed by the growing cells, so, that when the pad is removed, the bioabsorbable material had been absorbed, and the growing cells were not disturbed. The pad is replaced, if necessary, either by a conventional pad or by a matrix containing pad, as deemed therapeutically necessary.

EXAMPLE V

A bioabsorbable branched polymer, similar to that described in U.S. Pat. No. 5,578,662 issued to Bennet et al., forms the pad. The general principles of V.A.C.® therapy are followed with the bioabsorbable branched polymer pad substituted for the conventional pad. During the expected duty cycle of the pad, the pad is absorbed by the growing cells, so that there is no need to replace the pad and disturb the wound site. If further treatment is deemed necessary, a conventional pad, or an additional matrix containing pad, or an additional bioabsorbable branched polymer pad may be placed in the wound site, and V.A.C.® therapy continued.

While the foregoing description is exemplary of the preferred embodiment of the present invention, those of ordinary skill in the relevant arts will recognize the many variations, alterations, modifications, substitutions and the like are readily possible, especially in light of this description and the accompanying drawings. In any case, because the scope of the present invention is much broader than any particular embodiment, the foregoing detailed description should not be construed as a limitation of the scope of the present invention, which is limited only by the claims that are drawn hereto.

We claim:

1. A biocompatible wound dressing, comprising:
   a biocompatible pad shaped to conform to a wound site;
   an air-tight seal removably adhered to said pad;
   a negative pressure source in fluid communication with said pad;
   an ultra-low density fused-fibrous ceramic removably connected to the wound-contacting surface of the pad and adapted to act as a scaffold to facilitate cellular growth from the wound through ceramic.

2. The biocompatible wound dressing of claim 1 wherein the biocompatible pad comprises an open-cell reticulated porous foam adhered to non-wound contacting surfaces of said ceramic.

3. The biocompatible wound dressing of claim 1, further comprising a flexible tube communicating between said pad and said negative pressure source.

4. The biocompatible wound dressing of claim 3 further comprising a removable canister in fluid communication between said pad and said negative pressure source.

5. A biocompatible wound dressing comprising:
   a pad comprised of a non-biosorbable substrate and an ultra-low density fused-fibrous ceramic, the pad being shaped to conform to a wound site, the ultra low-density fused-fibrous ceramic adapted to be absorbed or included by the wound, the ceramic being removably connected to the wound-contacting surface of the pad and adapted to allow cellular growth through the ceramic;
   an air-tight seal removably adhered to said pad; and
   a negative pressure source in fluid communication with said ceramic.

6. The biocompatible wound dressing of claim 5 further comprising a flexible tube communicating between said pad and said negative pressure source.

7. The biocompatible wound dressing of claim 6 further comprising a removable canister in fluid communication between said pad and said negative pressure source.

8. A biocompatible wound dressing comprising:
   a first pad comprised of a bioabsorbable or includable cell-growth enhancing matrix, shaped to conform to a wound site;
   the bioabsorbable or includable cell-growth enhancing matrix comprising porous, highly reticulated material formed into a plurality of sections, the matrix being adapted to contact the wound surface and to be absorbed or included by the wound;
   an airtight seal removably adhered to said pad;
   a negative pressure source in fluid communication with said pad;
   a second pad comprised of a bioabsorbable cell-growth enhancing matrix, adapted to connect to the surface of the first pad opposite the wound-facing surface and to cover the first pad when the first pad is partially absorbed or included by the wound; and
   the bioabsorbable cell-growth enhancing matrix of the second pad comprising porous, highly reticulated material formed into a plurality of sections, the matrix being adapted to contact the wound surface and to be absorbed or included by the wound;
   wherein the bioabsorbable cell growth enhancing matrix of the second pad is adapted to facilitate cellular growth from the wound through the matrix;
   wherein the matrix of the first pad is adapted to facilitate cellular growth from the wound through the matrix.

9. The biocompatible wound dressing of claim 8 further comprising a removable canister in fluid communication between said pad and said negative pressure source.

10. The biocompatible wound dressing of claim 12 further comprising a removable canister in fluid communication between said pad and said negative pressure source.

11. The biocompatible wound dressing of claim 8, further comprising a third pad comprised of a non-bioabsorbable substrate removable coupled to the second pad, wherein the substrate defines a plurality of holes remote from the cell-growth enhancing matrices.

12. A biocompatible wound dressing comprising:
   a pad comprised of a non-bioabsorbable substrate, and a bioabsorbable cell-growth enhancing matrix removably coupled to the non-bioabsorbable substrate, the pad being shaped to conform to a wound site;
   the cell-growth enhancing matrix comprising reticulated porous material formed into a plurality of sections and implanted into the substrate in the central portion of the pad, the matrix being adapted to contact the wound surface and to be absorbed or included by the wound;
   the substrate defining a plurality, of holes remote from the bioabsorbable cell-growth enhancing matrix;
   an airtight seal removably adhered to the pad; and
   a negative pressure source in fluid communication with the pad.

* * * * *

UNITED STATES PATENT AND TRADEMARK OFFICE
CERTIFICATE OF CORRECTION

PATENT NO. : 7,070,584 B2
APPLICATION NO. : 10/075743
DATED : July 4, 2006
INVENTOR(S) : Royce Johnson and David Tumey It is certified that error appears in the above-identified patent and that said Letters Patent is hereby corrected as shown below:

Column 7, line 45 replace "biocompatible" with --biocompatible--
Related U.S. Application Data replace "60/269,957" with --60/269,657--

Signed and Sealed this

Twelfth Day of September, 2006

JON W. DUDAS
*Director of the United States Patent and Trademark Office*

UNITED STATES PATENT AND TRADEMARK OFFICE
CERTIFICATE OF CORRECTION

| | | |
|---|---|---|
| PATENT NO. | : 7,070,584 B2 | Page 1 of 1 |
| APPLICATION NO. | : 10/075743 | |
| DATED | : July 4, 2006 | |
| INVENTOR(S) | : Royce Johnson and David Tumey | |

It is certified that error appears in the above-identified patent and that said Letters Patent is hereby corrected as shown below:

Column 7, line 46 replace "biocompatible" with --biocompatible--
Related U.S. Application Data replace "60/269,957" with --60/269,657--

This certificate supersedes Certificate of Correction issued September 12, 2006.

Signed and Sealed this

Twelfth Day of December, 2006

JON W. DUDAS
*Director of the United States Patent and Trademark Office*

UNITED STATES PATENT AND TRADEMARK OFFICE
CERTIFICATE OF CORRECTION

PATENT NO. : 7,070,584 B2  Page 1 of 1
APPLICATION NO. : 10/075743
DATED : July 4, 2006
INVENTOR(S) : Royce Johnson and David Tumey It is certified that error appears in the above-identified patent and that said Letters Patent is hereby corrected as shown below:

Column 6, line 43, replace "Lin" with --Liu--

Signed and Sealed this

First Day of May, 2007

JON W. DUDAS
*Director of the United States Patent and Trademark Office*